United States Patent
Laha et al.

(10) Patent No.: US 10,658,080 B2
(45) Date of Patent: May 19, 2020

(54) METHOD FOR MONITORING BEHAVIOUR OF A PATIENT IN REAL-TIME USING PATIENT MONITORING DEVICE

(71) Applicant: Wipro Limited, Bangalore (IN)

(72) Inventors: Sumanta Laha, Begampur (IN); Sreevidya Khatravath, Hyderabad (IN)

(73) Assignee: Wipro Limited, Bangalore (IN)

( * ) Notice: Subject to any disclaimer, the term of this patent is extended or adjusted under 35 U.S.C. 154(b) by 774 days.

(21) Appl. No.: 14/979,794

(22) Filed: Dec. 28, 2015

(65) Prior Publication Data

US 2017/0140119 A1    May 18, 2017

(30) Foreign Application Priority Data

Nov. 13, 2015    (IN) ............................ 6134/CHE/2015

(51) Int. Cl.
*G16H 40/63*        (2018.01)
*A61B 5/0402*      (2006.01)
(Continued)

(52) U.S. Cl.
CPC .............. *G16H 40/63* (2018.01); *G06F 19/00* (2013.01); *G06K 9/00335* (2013.01); *G06K 9/6284* (2013.01); *G16H 50/70* (2018.01); *A61B 5/01* (2013.01); *A61B 5/0402* (2013.01); *A61B 5/082* (2013.01); *A61B 5/11* (2013.01); *A61B 5/14542* (2013.01); *A61B 5/7264* (2013.01); *G06K 2009/00738* (2013.01)

(58) Field of Classification Search
CPC ..................................................... G16H 50/70
See application file for complete search history.

(56) References Cited

U.S. PATENT DOCUMENTS 9,047,746 B1    6/2015  Euliano, II et al.
2002/0099273 A1*  7/2002  Bocionek ............... A61B 5/411
                                                                600/300
(Continued)

FOREIGN PATENT DOCUMENTS

WO    WO-2017032873 A2 *  3/2017  ............. A61B 5/746

OTHER PUBLICATIONS

Extended European Search Report issued in the European Patent Office in counterpart European Application No. 16173303.5, dated Sep. 7, 2017, 9 pages.

*Primary Examiner* — Sheetal R Paulson
(74) *Attorney, Agent, or Firm* — Finnegan, Henderson, Farabow, Garrett & Dunner, LLP

(57) ABSTRACT

The present disclosure relates to a method for monitoring behaviour of a patient in real-time. The method comprises receiving, by a patient monitoring device, data related to the patient from one or more sources. Thereafter, the patient monitoring device classifies the received data into one or more categories based on one or more rules. Further, the patient monitoring device correlates the categorized data to identify one or more activity patterns corresponding to the patient, wherein each of the one or more activity patterns are associated with an activity performed by the patient at predefined time intervals. The patient monitoring devices compares the activity pattern with predefined activity patterns and detects abnormal behaviour of the patient if the identified activity pattern is different from one or more predefined activity patterns corresponding to the patient.

12 Claims, 5 Drawing Sheets

(51) Int. Cl.

| | |
|---|---|
| *A61B 5/145* | (2006.01) |
| *A61B 5/01* | (2006.01) |
| *A61B 5/08* | (2006.01) |
| *A61B 5/11* | (2006.01) |
| *A61B 5/00* | (2006.01) |
| *G16H 50/70* | (2018.01) |
| *G06K 9/00* | (2006.01) |
| *G06K 9/62* | (2006.01) |
| *G06F 19/00* | (2018.01) |

(56) References Cited

U.S. PATENT DOCUMENTS

| | | |
|---|---|---|
| 2006/0061472 A1 | 3/2006 | Lovoi et al. |
| 2006/0210626 A1 | 9/2006 | Spaeder |
| 2014/0009262 A1 | 1/2014 | Robertson et al. |
| 2015/0119739 A1* | 4/2015 | Kurzweil ............ A61B 5/0452 600/515 |
| 2017/0039480 A1* | 2/2017 | Bitran ................ G06F 19/3481 |

* cited by examiner

METHOD FOR MONITORING BEHAVIOUR OF A PATIENT IN REAL-TIME USING PATIENT MONITORING DEVICE

TECHNICAL FIELD

The present subject matter is related, in general to monitoring system, and more particularly, but not exclusively to a method and a system, for monitoring behaviour of a patient in real-time.

BACKGROUND

Generally in nursing homes and in hospitals, nursing staff assess, treat, support and care for patients. This mainly involves discussing, planning and carrying out nursing care to improve patients' health, continuously monitoring patients' conditions and recording important changes, giving medication and monitoring its effect on patients and educating patients and their families about health needs and life style changes. However, the patient may still carry on with same normal life style in hospital or during recovery period which may lead to critical circumstances for patient's health. Therefore, keen attention and monitoring of patients in real-time is required for better treatment and recovery.

At present, various conventional patient monitoring techniques are available and are focused on movement of patients, identifying habits of patient like smoking and drinking, identifying respiratory problems with sensors and using video footage to observe patient activities. However, the conventional techniques lack correlation of the data to identify the problem related to the patient at any given point of time. The conventional techniques mainly rely on stand-alone reports of health monitoring systems, sensors, videos etc. Standalone reports cannot detect the cause of a particular behaviour of the patient and also do not disclose the recovery period of any given symptom. The standalone reports do not provide sufficient information to predict the upcoming disease symptoms. As a result of which real-time notifications related to the abnormal behaviour of the patient cannot be provided to the one or more caretakers (alternatively referred as receiving entities) of the patient, to stop the patient from performing the activity which is not prescribed by the doctor or the nursing staff. As an example, the standalone EGG report may indicate the patient having a heart attack but it does not indicate the reason behind the heart attack.

One of the conventional techniques discloses a system and method for real-time monitoring and management of patients from a remote location. The system comprises one or more patient's communication devices configured to facilitate users to enter patient related data using a healthcare application. The system further comprises an analysing and processing module for processing the patient related data. The analysing and processing module is further configured to send alerts to physicians. But this technique does not involve correlating patient related data to identify different behaviour patterns of the patient. Also this technique does not disclose the aspect of providing real-time alerts to care takers of patient when patient is performing an abnormal activity which affects the recovery of the patient.

Currently, the existing solutions are not able to infer the behaviour of patient in real time, correlate the information from health monitoring devices to give precaution and remedy suggestions. The existing solutions cannot generate real time alert to nursing station or the caretakers while the patient is performing an abnormal activity.

Therefore, there is a need for a system which can detect specific food, sleeping patterns using video, sound based inputs and correlate all the data to identify different behaviour patterns of the patient. Also, a system which renders precaution remedies and provide alerts to the patient's caretakers at real-time.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

Disclosed herein is a method for monitoring behaviour of a patient in real-time using a patient monitoring device. The patient monitoring device receives data related to the patient from one or more sources and correlates the data to identify the abnormal behaviour of the patient to render precaution remedies and to provide alerts to the patient's caretakers in real-time.

Accordingly, the present disclosure relates to a method for monitoring behaviour of a patient in real-time. The method comprises receiving, by a patient monitoring device, data related to the patient from one or more sources. Thereafter, the patient monitoring device classifies the received data into one or more categories based on one or more rules. Further, the categorized data is correlated by the patient monitoring device to identify one or more activity patterns corresponding to the patient, wherein each of the one or more activity patterns are associated with an activity performed by the patient at predefined time intervals. Upon correlating the categorized data, the patient monitoring device detects abnormal behaviour of the patient if the one or more identified activity patterns are different from one or more predefined activity patterns corresponding to the patient.

Further, the present disclosure relates to a patient monitoring device for monitoring behaviour of a patient in real-time. The patient monitoring device comprises a processor and a memory communicatively coupled to the processor, wherein the memory stores the processor-executable instructions, which, on execution, causes the processor to receive data related to the patient from one or more sources. Upon receiving the data, the processor classifies the received data into one or more categories based on one or more rules. Further, the processor correlates the categorized data to identify one or more activity patterns corresponding to the patient, wherein each of the one or more activity patterns are associated with an activity performed by the patient at predefined time intervals. Finally, the processor detects abnormal behaviour of the patient if the one or more identified activity patterns are different from one or more predefined activity patterns corresponding to the patient.

Further, the present disclosure comprises a non-transitory computer readable medium including instructions stored thereon that when processed by at least one processor causes a patient monitoring device to perform operations comprising receiving data related to the patient from one or more sources. The instructions further cause the processor to classify the received data into one or more categories based on one or more rules stored in a memory associated to the patient monitoring system. Thereafter, the instructions cause the processor to correlate the categorized data to identify one or more activity patterns corresponding to the patient, wherein each of the one or more activity patterns are associated with an activity performed by the patient at predefined time intervals. Further, the instructions cause the processor to detect abnormal behaviour of the patient if the one or more identified activity patterns are different from one or more predefined activity patterns corresponding to the patient.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1:
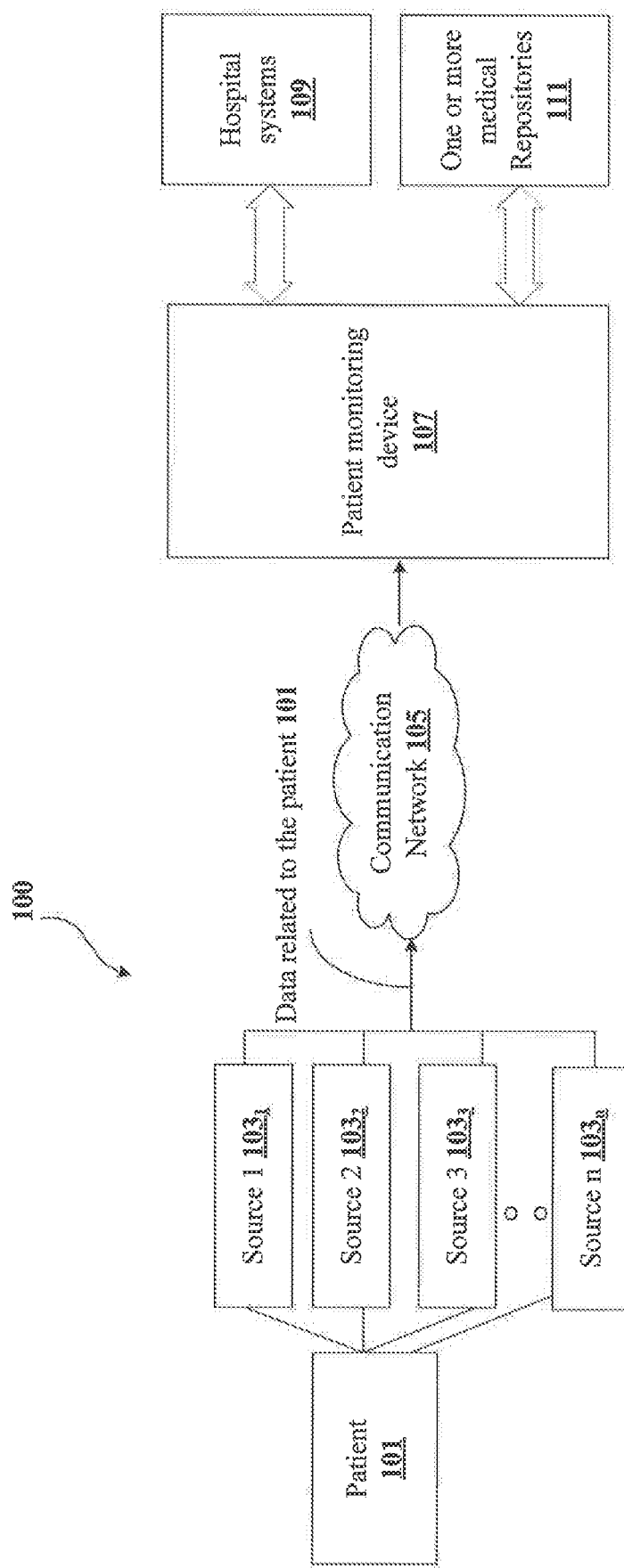
FIG. 1 shows an exemplary architecture for monitoring behaviour of a patient in real-time in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The present disclosure relates to a method for monitoring behaviour of a patient in real-time using a patient monitoring device. The patient monitoring device receives data related to the patient from one or more sources configured near the patient. The received data is classified into one or more categories based on one or more rules. The one or more rules are stored in a memory associated with the patient monitoring device. The categorized data is further correlated to identify one or more activity patterns related to the patient. The one or more identified activity patterns are compared with one or more predefined activity patterns to detect the one or more identified activity patterns that are different from the one or more predefined activity patterns. Then an abnormal behaviour of the patient, corresponding to the different one or more identified activity patterns is detected and a notification is provided to one or more recipients of the patient.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 shows an exemplary architecture for monitoring behaviour of a patient in real-time using a patient monitoring device in accordance with some embodiments of the present disclosure.

The architecture 100 comprises one or more sources, source 1 $103_1$ to source a $103_n$ (collectively referred to as sources 103), a communication network 105, a patient monitoring device 107, a hospital system 109 and one or more medical repositories 111. The one or more sources 103 are at least one of an audio recording device, an image capturing device, a video capturing device and one or more medical devices. As an example the audio recording device may include, but not limited to, a microphone, a dictaphone and a mobile phone. As an example, the image capturing device may include, but not limited to, a camera, a mobile phone and a tablet. As an example the video capturing device may include, but not limited to, a camera, a mobile phone and a tablet. As an example the one or more medical devices may be an ElectroCardioGram (ECG), a pulse oximeter, temperature sensor, a capnograph monitor etc. The communication network 105 may include at least one of wired communication network and wireless communication network.

Figure 2A:
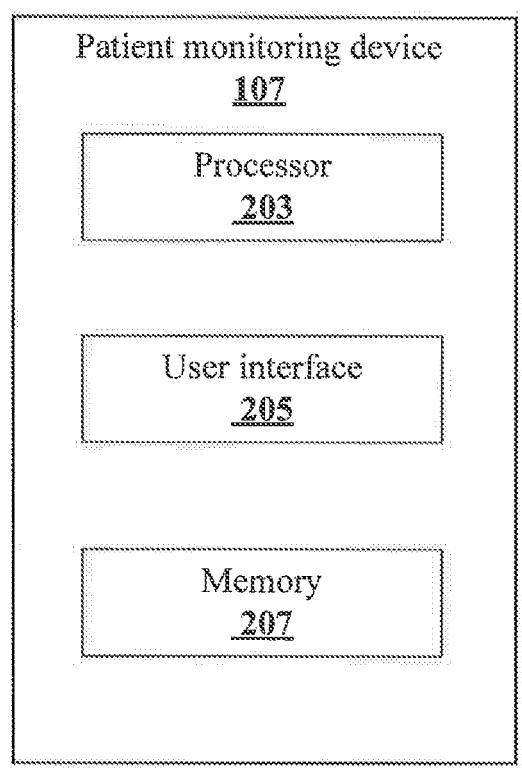
FIG. 2a shows a block diagram of a patient monitoring device for monitoring behaviour of a patient in real-time in accordance with some embodiments of the present disclosure.

The one or more sources 103 are configured to monitor the behaviour of the patient 101. As an example, the audio recording device is configured to capture voice data of the patient 101. The image capturing device may capture images or activities of the patient 101. The one or more sources 103 may be configured either inside the room where the patient 101 is present or outside the room of the patient 101. As an example, a camera may be fixed inside the room of the patient 101 to capture the video of one or more activities performed by the patient 101 and the camera may also be fixed outside the room of the patient 101 to monitor incidents such as people entering the room of the patient 101 after visiting hours etc. In one embodiment, the patient 101 is monitored in a hospital environment, wherein the one or more sources are configured in each patient's room. In another embodiment, the patient 101 may be monitored at, patient's residence itself, wherein the one or more sources 103 are configured in the residence of the patient 101 to capture the data related to the patient 101. Upon monitoring the patient 101 by the one or more sources 103, data related to the patient 101 is transmitted to the patient monitoring device 107 through the communication network 105. The patient monitoring device 107 comprises a processor 203, a user interlace 205 and a memory 207 as shown in FIG. 2*a*. The processor 203 is configured to receive the data related to the patient 101 from the one or more sources 103, The received data is displayed on the user interface 205. Upon receiving the data related to the patient 101, the processor 203 classifies the received data into one or more categories based on one or more rules stored in the memory 207. The one or more rules are either predefined or dynamically updated. The one or more categories may be an audio category, video category, image category and medical category. In medical category, the medical reports are further categorized based on the type of the report, such as ECG report. Blood pressure report, blood-sugar level report etc. In one embodiment, the one or more rules may define the format in which the data related to the patient 101 should be stored, order in which the data related to the patient 101 should be collected etc.

As an example, the one or more rules may define that the audio data related to the patient 101 should be stored under audio category in MP3 format, video data related to the patient should be stored under video category in MP4 format, image data related to the patient 101 should be stored under image category in PEG format etc. In one embodiment, the data related to the patient 101 is stored in the memory 207 in accordance with the time at which the captured one or more activities were performed by the patient 101.

In an embodiment, classifying the data further comprises filtering the data based on the one or more rules. The filtering is performed to retain the data required for monitoring the behaviour of the patient 101 and discard rest of the data which is irrelevant for patient monitoring. As an example, if the video capturing device has captured a video of the patient 101 sleeping for 5 hours wherein no other activity is performed (for example snoring or walking while sleeping etc.), then the video is discarded as no other activity is performed but the number of hours the patient 101 slept for i.e. 5 hours, is retained and stored, as this information is required for monitoring the behaviour of the patient 101. The processor 203 decides which data should be retained and which data should be discarded, based on the one or more rules. The one or more rules can be dynamically updated based on the one or more activities performed by the patient 101, the time consumed to perform the one or more activities and the predefined one or more rules. Upon classifying the data, the processor 203 correlates the categorized data for identifying the one or more activity patterns corresponding to the patient 101 i.e. the processor 203 correlates the audio data, the video data, the image data and the medical data received from the one or more sources 103. Each of the one or more activity patterns are associated with an activity performed by the patient 101 at predefined time intervals. The categorized data is converted into text format based on predefined configuration information stored in the memory 207, since correlation of the categorized data can be performed only when the data related to the patient 101 is in a single format. As an example, the medical data prescribes medicine intake by the patient 101 at predefined time intervals. The processor 203 correlates the medical data with the video data of the patient 101 at the predefined time intervals, to check whether the patient 101 is taking the prescribed medicine at the scheduled time intervals or not. Further in the example, the patient's recovery is measured by correlating previous medical reports of the patient 101 with present medical reports of the patient 101. In one embodiment, the one or more activity patterns may be food intake patterns, medicine intake patterns, breathing pattern, sleeping patterns etc. As an example, if the patient 101 is suffering from asthma, prescribing aspirin (a medicine), has side effects such as coughing, wheezing, itchy skin, red eyes, swollen cheeks and lips and runny nose on the patient 101. Therefore, prescribing aspirin to the patient 101 causes more breathing problems, which is recorded as, one of the one or more activity patterns of the patient 101. Upon identifying the one or more activity patterns of the patient 101, the one or more activity patterns are compared with one or more predefined activity patterns corresponding to the patient 101, stored in the memory 207. As an example, the patient 101 has been treated for a fractured hand. According to the doctor's instructions, the patient 101 is not supposed to lift materials for 10 days. The normal movement of the fractured hand is stored as the predefined activity of the patient 101 for the next 10 days. Lifting the hand for performing exercise is also stored as a predefined activity of the patient 101. If the identified one or more activity patterns are different from the one or more predefined activity patterns, then the abnormal behaviour of the patient 101 corresponding to the identified indifferent activity pattern is detected. Consider a scenario wherein, the patient 101 lifted a hag with the fractured hand, which is not the normal activity or the predefined activity to be performed by the patient 101. Upon comparing the identified activity pattern with the predefined activity pattern of the patient 101, the identified activity pattern is different from the predefined activity pattern. Therefore, lifting the hag is detected as the abnormal behaviour of the patient 101. Upon detecting the abnormal behaviour of the patient 101, the processor 203 provides a notification related to the abnormal behaviour of the patient 101 to the one or more receiving entities. As an example one or more receiving entities may include, but not limited to, one or more caretakers of the patient 101 such as the doctor, a nurse, friend of the patient, relatives of the patient etc.

In an embodiment, the processor 203 compares the abnormal behaviour of the patient 101 with a symptom learning table stored in the memory 207, to identify one or more symptoms corresponding to the detected abnormal behaviour of the patient 101. The symptom learning table is extracted from one or more medical repositories 111 associated with the patient monitoring device 107. The one or more medical repositories 111 is a data system comprising information such as patient records from different healthcare organizations, latest updates in the healthcare systems and information related to one or more causes, symptoms, case studies and one or more remedies of a specific disorder. Each of the one or more symptoms in the symptom learning table is associated with a precaution measure. The precaution measure corresponding to the identified one or more symptoms is indicated to the one or more receiving entities. Upon indicating the one or more symptoms, one or more remedies corresponding to the abnormal behaviour of the patient 101 are identified by the processor 203. The information related to the remedies is stored in the memory 207. The one or more remedies are extracted from the one or more medical repositories 111. The patient monitoring device 107 is also associated with hospital systems 109. The hospital system 109 is a platform handling patient's data such as laboratory data, radiology data, cardiology reporting, clinical data repository etc. which is required for diagnosis and treatment of the patient 101.

Scenario-1

As an example, consider that the patient 101 is suffering from a disease "chicken pox" (chicken pox is a disease causing a mild fever and a rash of itchy inflamed pimples which turn to blisters). The one or more sources 103 are configured near the patient 101 to record and capture the data related to the patient 101. As per the doctor's instructions which have been recorded in the medical data of the patient 101, the patient 101 is not supposed to take any food items except curd rice and also the patient 101 is not supposed to scratch the blisters formed on the body.

The one or more predefined activity patterns of the patient 101 recorded are in accordance with the doctor's instructions i.e. patient 101 eats only curd rice and does not scratch the blisters formed on the body.

The video capturing device captures the patient 101 eating spicy food. The video data comprising captured video of the patient 101 eating spicy food is received by the patient monitoring device 107 through the communication network 105. The processor 203 correlates the received video data with the medical data. Based on the correlated data, the processor 203 recognizes the activity pattern of the patient 101 and compares the identified activity pattern with the predefined activity pattern of the patient 101. The processor 203 detects that the identified activity pattern is different from the predefined activity pattern. Therefore, the abnormal behaviour of the patient 101 is identified by the patient monitoring device 107. The patient monitoring device 107 provides a notification in real-time to the one or more recipients regarding the abnormal behaviour of the patient 101. The patient monitoring device 107 also compares the abnormal behaviour of the patient 101 with symptom learning table to identify one or more symptoms corresponding to the abnormal behaviour pattern and indicate a precaution measure to the one or more recipients. The one or more symptoms corresponding to the abnormal behaviour pattern identified for the patient 101 may be excessive skin irritation and increase in blisters formed on the body. The precaution measure associated with the identified symptoms may be not to consume spicy food and to not scratch the blisters. Further, the processor 203 indicates one or more remedies to the one or more recipients for taking immediate action. The one or more remedies indicated to the one or more recipients may be to apply doctor prescribed lotion on the blisters to reduce the skin irritation, to trim the nails of the patient 101 to avoid any further infection, to drink lots of water and to consume only curd rice.

Scenario-2

As an example, consider the patient 101 is suffering from disease "diabetes" (a disorder of the metabolism that affects body's ability to produce or use insulin). As per the doctor's instructions which have been recorded in the medical data, the patient 101 is supposed to exercise from 4:30 PM to 6:00 PM.

The one or more predefined activity patterns of the patient 101 recorded are in accordance with the doctor's instructions. As an example two predefined activity patterns are instructed for this patient 101, One of the predefined activity patterns is the patient 101 exercises from 4:30 PM to 6:00 PM and the other predefined activity pattern is the food plan at predefined time intervals.

The video capturing device captures the patient 101 sleeping and the audio recording device records the patient 101 snoring in his sleep at 4:30 PM, The video data and the audio data, comprising the captured video and the recorded audio of the patient 101 snoring in his sleep, is received by the patient monitoring device 107 through the communication network 105. The processor 203 correlates the received video data, audio data with the stored medical data. Based on the correlated data, the processor 203 recognizes the activity pattern of the patient 101 and compares the identified activity pattern with the predefined activity pattern of the patient 101. The processor 203 detects that the identified activity pattern is different from the predefined activity pattern. Therefore, the abnormal behaviour of the patient 101 is identified by the patient monitoring device 107. The patient monitoring device 107 provides a notification to the one or more recipients regarding the abnormal behaviour of the patient 101. The patient monitoring device 107 also compares the symptom learning table to identify one or more symptoms corresponding to the abnormal behaviour pattern and indicate a precaution measure to the one or more recipients. The one or more symptoms corresponding to the abnormal behaviour pattern identified for the patient 101 may be, increased blood glucose levels, improper usage of insulin in the metabolism, increase in body weight and weakness. The precaution measure associated with the identified symptoms may be, to keep the blood sugar level in control, to keep the cholesterol level in control and to consume balanced diet at regular intervals of time. Further, the processor 203 indicates one or more remedies to the one or more recipients for taking immediate action. The one or more remedies indicated to the one or more recipients may be, to wake up the patient from sleep and instruct him to exercise according to the schedule to avoid further complications.

In an embodiment, upon indicating the one or more remedies for the one or more recipients of the patient 101, the processor 203 monitors patient's health continuously. If the patient's health is not improving even after following the remedies, the processor 203 recognizes the activity patterns of the patient 101, to find the reasons for non-improvement in the patient's health using natural language processing techniques. As an example, if the patient 101 is suffering from viral fever, the initial level of virus in the patient's blood is determined. Upon determining the initial level of virus, the blood reports of the patient 101 are compared on a day to day basis to understand the increase or decrease in the level of virus. If the level of virus decreases compared to the initial level, the patient 101 is recovering. If the level of virus increases compared to the initial level then the processor 203 detects that the patient's health is not improving and therefore suggests different remedies to the patient 101.

Figure 2B:
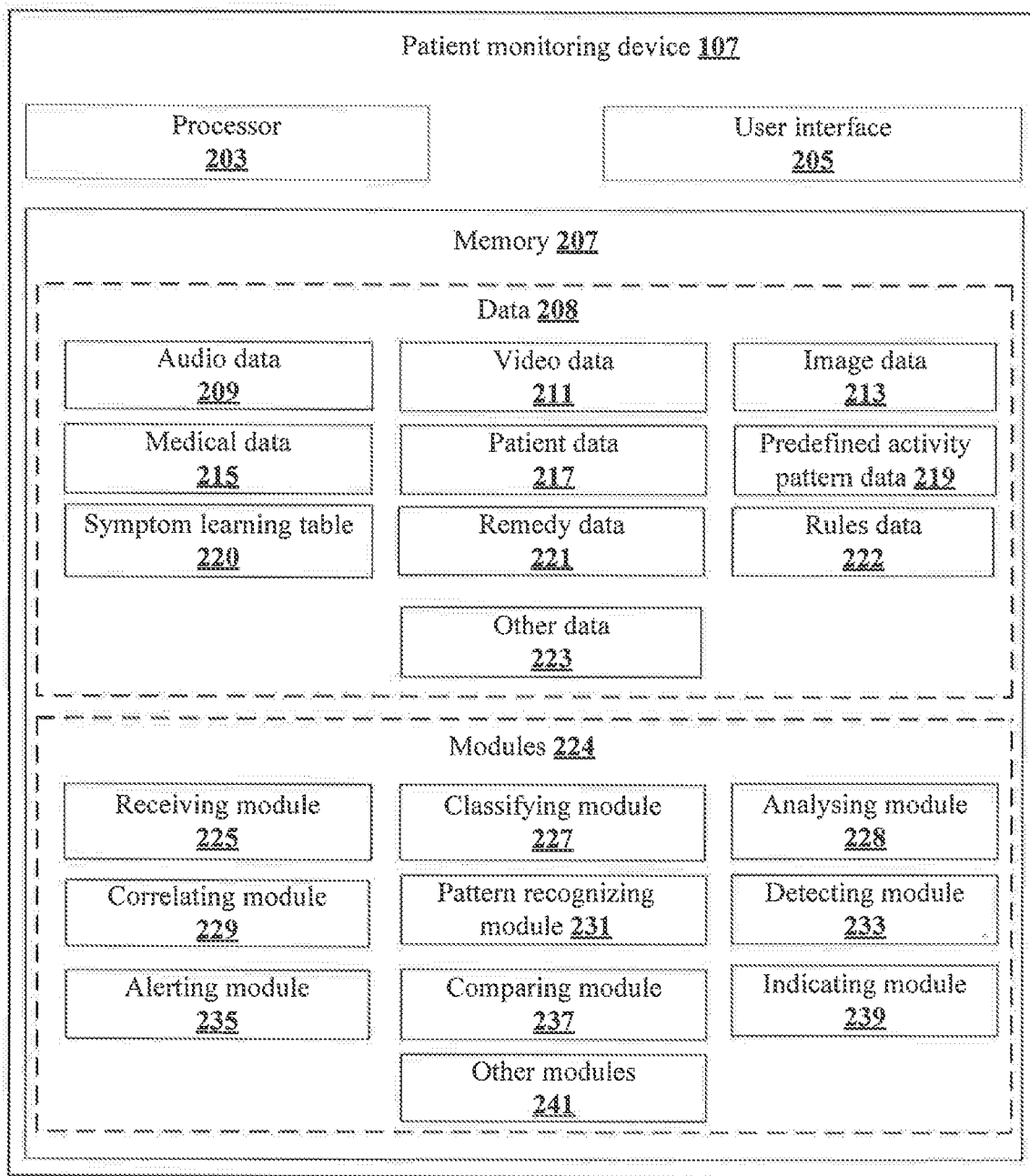
FIG. 2b shows a detailed block diagram of a patient monitoring device for monitoring behaviour of a patient in real-time in accordance with some embodiments of the present disclosure.

FIG. 2b shows a detailed block diagram of a patient monitoring device for monitoring behaviour of a patient in real-time in accordance with some embodiments of the present disclosure.

In one implementation, the patient monitoring device 107 receives data related to the patient 101 from one or more sources. As an example, the data is stored in a memory 207 associated with the patient monitoring device 107. In an embodiment, the data includes audio data 209, video data 2111, image data 213, medical data 215, patient data 217, predefined activity pattern data 219, symptom learning table 220, remedy data 221, rules data 222 and other data 223. The one or more sources may include but not limited to audio recording device, video capturing device, image capturing device and one or more medical devices. In the illustrated FIG. 2b, one or more modules 224 stored in the memory 207 are described herein in detail.

In one embodiment, the data may be stored in the memory 207 in the form of various data structures. Additionally, the aforementioned data can be organized using data models, such as relational or hierarchical data models. The other data 223 may store data, including temporary data and temporary files, generated by modules 224 for performing the various functions of the patient monitoring device 107.

In an embodiment, the audio data 209 is received from the audio recording device. The audio recording device may be configured inside room of the patient 101. The audio recording device may include but not limited to a microphone, a dictaphone and a mobile phone. The audio data 209 comprises audio feed associated with the patient 101 and stored in the memory 207 under audio category. As an example, the audio data 209 may be, the patient 101 moaning in sleep, nursing staff's advice to the patient 101, doctor's oral prescription to the patient 101 etc.

In an embodiment, the video data 211 is received from the video capturing device configured inside and outside the room of the patient 101. The video capturing device may include but not limited to, a camera, a mobile phone and a tablet. The video data 211 comprises video feed associated with the patient 101 and stored in the memory 207 under video category. As an example, the video data 211 may be, one or more activities performed by the patient 101, people entering the patient's ward, medicines given to the patient 101 etc. As an example, the one or more activities may be the patient 101 performing exercises as advised by the nursing staff, the patient 101 taking medicines at prescribed time, patient 101 trying to walk inside the room etc.

In an embodiment, the image data 213 is received from the image capturing device configured inside and outside the room of the patient 101. The image capturing device may include, but not limited to a camera, a mobile phone and a tablet. The image data 213 comprises images associated with the patient 101 and stored in the memory 207 under image category. As an example, the image data 213 may be image of medicine intake by the patient 101, image of doctor examining the patient 101, image of the X-RAY related to the patient 101 etc.

In an embodiment, the medical data 215 is received from the one or more medical devices. As an example the one or more medical devices may be an ElectroCardioGram (ECG), a pulse oximeter, temperature sensor, a capnograph monitor etc. The medical data 215 comprises one or more medical reports related to the patient 101, one or more readings recorded by the one or more medical devices etc. which are stored in the memory 207 under medical category. The one or more medical reports comprise the present medical reports and the past medical reports related to the patient 101. As an example, the one or more medical reports may be ECG reports, blood sugar level reports etc. the one or more readings may be the Blood Pressure (BP) reading representing either high BP or low BP, temperature reading from the temperature sensor etc.

In an embodiment, the patient data 217 is received from the patient 101 and sometimes from one or more medical reports of the patient 101. The patient data 217 comprises information such as name, age and sex of the patient 101, lifestyle of the patient 101 such as eating habits, exercising habits, smoking habits, drinking habits etc. The patient data 217 also comprises staff's concern about the patient 101, specific information given by the patient 101 which is not present in the one or more medical reports, one or more queries of the patient 101. The staff may comprise at least one of a nurse and a doctor.

In an embodiment, the predefined activity pattern data 219 comprises the data related one or more activities defined for the patient 101. The one or more activity patterns identified currently are compared with the predefined activity pattern data 219 to detect abnormal behaviour of the patient 101.

In an embodiment, the symptom learning table 220 comprises the list of one or more symptoms corresponding to certain behaviours of the patient 101 and each of the one or more symptoms is associated with a precaution measure. The symptom learning table 220 is extracted from the one or more medical repositories 111. The detected abnormal behaviour of the patient 101 is compared with the symptom learning table 220 to identify the one or more symptoms corresponding to the abnormal behaviour. Based on the one or more symptoms identified, the precaution measure corresponding to the identified one or more symptoms is indicated to the one or more receiving entities. As an example one or more receiving entities may include, but not limited to, one or more caretakers of the patient 101 such as the doctor, a nurse, friend of the patient, relatives of the patient etc.

In an embodiment, the remedy data 221 comprises one or more remedies for the identified abnormal behaviour of the patient 101. The one or more remedies are corresponding to the abnormal behaviour of the patient 101 are identified by the processor 203 from remedy data stored in the memory 207. The remedy data 221 is extracted from the one or more medical repositories 111.

As an example, if the patient 101 is feeling uncomfortable in his sleep and the body temperature is high, the processor 203 identifies one or more symptoms corresponding to the behaviour of the patient 101. The symptom learning table identifies the disorder to be fever and identifies one or more symptoms to be excessive sweating, headache, weakness, cough and loss of appetite. The processor 203 provides the precaution measures associated with the one or more symptoms. In this scenario, the precaution measures for the patient 101 may be to stay in a well-ventilated room, to drink more water frequently, to eat non-oily food like bread, curd rice etc. Upon identifying the one or more symptoms and the precaution measures, the processor 203 provides the one or more remedies corresponding to the identified symptoms. In this scenario, the one or more remedies suggested to the patient 101 may be to stay indoors, to drink more water, to take proper medication to reduce fever such as a paracetamol, to stay away from dust etc.

In an embodiment, the rules data 222 comprises the one or more rules applied for classifying the data. The rules data 222 defines the format in which the data related to the patient 101 should be stored, order in which the data related to the patient 101 should be collected etc. As an example, the one or more rules may mention that the audio data 209 related to the patient 101 should be stored under audio category in MP3 format, video data 211 related to the patient 101 should be stored under video category in MP4 format, image data related to the patient 101 should be stored under image category in PEG format etc. In one embodiment, if the data collected from one or more sources is in the format other than the format specified in the one or more rules, then the collected data is converted into the specified format by the processor 203 and then stored in the memory 207. In one embodiment, the data related to the patient 101 is stored in the memory 207 in accordance with the time at which the captured one or more activities were performed by the patient 101. The rules data 222 comprises the one or more rules to filter the data such that only those data which are necessary monitoring the behaviour of the patient 101 is retained and rest of the data is discarded. The rules data 222 comprises the one or more rules for converting the collected data into text format before correlating the data. The one or more rules can be dynamically updated based on the one or more activities performed by the patient 101 and the time consumed to perform the one or more activities.

In an embodiment, the data stored in the memory 207 is processed by the modules 224 of the patient monitoring device 107. The modules 224 may be stored within the memory 207 as shown in the FIG. 2b. In an example, the modules 224, communicatively coupled to the processor 203, may also be outside the memory 207.

In an embodiment, the modules 224 may include, for example, a receiving module 225, a classifying module 227, a correlating module 229, a pattern recognizing module 231, a detecting module 233, an alerting module 235, a comparing module 237, an indicating module 239 and other modules 241. The other modules 241 may be used to perform various miscellaneous functionalities of the patient monitoring device 107. It will be appreciated that such aforementioned modules 224 may be represented as a single module or a combination of different modules.

In an embodiment, the receiving module 225 receives the data related to the patient 101 from the one or more sources 103 configured to monitor the behaviour of the patient 101 as explained in FIG. 1.

In an embodiment, the classifying module 227 categorizes the received data into one or more categories and then filters the received data based on one or more rules stored in the memory 207.

In an embodiment, the analysing module 228 analyses the categorized data based on one or more techniques. As an example, the video data 211 with one or more activities of the patient 101 is analysed using face recognition technique. If the patient 101 is on bedstead, the one or more activities of the patient 101 such as movement of head and limbs are analysed through image processing technique. The radial and axial movements of the body parts are detected using the image processing technique. Eating habits of the patient 101 are recorded and analysed using, but not limited to, Text analytic methods. Calorie values related to intake of each food item by the patient 101 is calculated and recorded using, but not limited to, combination of the image processing technique and one or more machine learning algorithms.

In an embodiment, the correlating module 229 correlates the audio data 209, the video data 211, the image data 213 and the medical data 215. The categorized data is converted into text format based on predefined configuration information stored in the memory 207, since correlation of the categorized data can be performed only when the data related to the patient 101 is in a single format.

In an embodiment, the pattern recognizing module 231 identifies one or more activity patterns based on correlation of the data. Each of the one or more activity patterns are associated with an activity performed by the patient 101 at predefined time intervals. In one embodiment, the one or more activity patterns may be food intake patterns, medicine intake patterns, breathing pattern, sleeping patterns etc. The identified one or more activity patterns are compared with the one or more predefined activity patterns of the patient 101, to identify the activity pattern which is different from predefined activity pattern. The abnormal behaviour corresponding to the different activity pattern is then detected by the detecting module 233.

In an embodiment, the alerting module 235 provides a notification related to the abnormal behaviour of the patient 101 to the one or more receiving entities. As an example one or more receiving entities may include, but not limited to, one or more caretakers of the patient 101 such as the doctor, a nurse, friend of the patient, relatives of the patient etc.

In an embodiment, the comparing module 237 compares the detected abnormal behaviour of the patient 101 with a symptom learning table 220 stored in the memory 207, to identify one or more symptoms corresponding to the detected abnormal condition of the patient 101. The symptom learning table 220 is extracted from one or more medical repositories 111 associated with the patient monitoring device 107. Each of the one or more symptoms in the symptom learning table 220 is associated with a precaution measure.

In an embodiment, the indicating module 239, indicates the precaution measure corresponding to the identified one or more symptoms to the one or more receiving entities. Further, the indicating module 239 indicates one or more remedies corresponding to the abnormal behaviour of the patient 101 to the one or more receiving entities for performing the required treatment to the patient 101 and for ensuring quick recovery of the patient 101.

Figure 3:
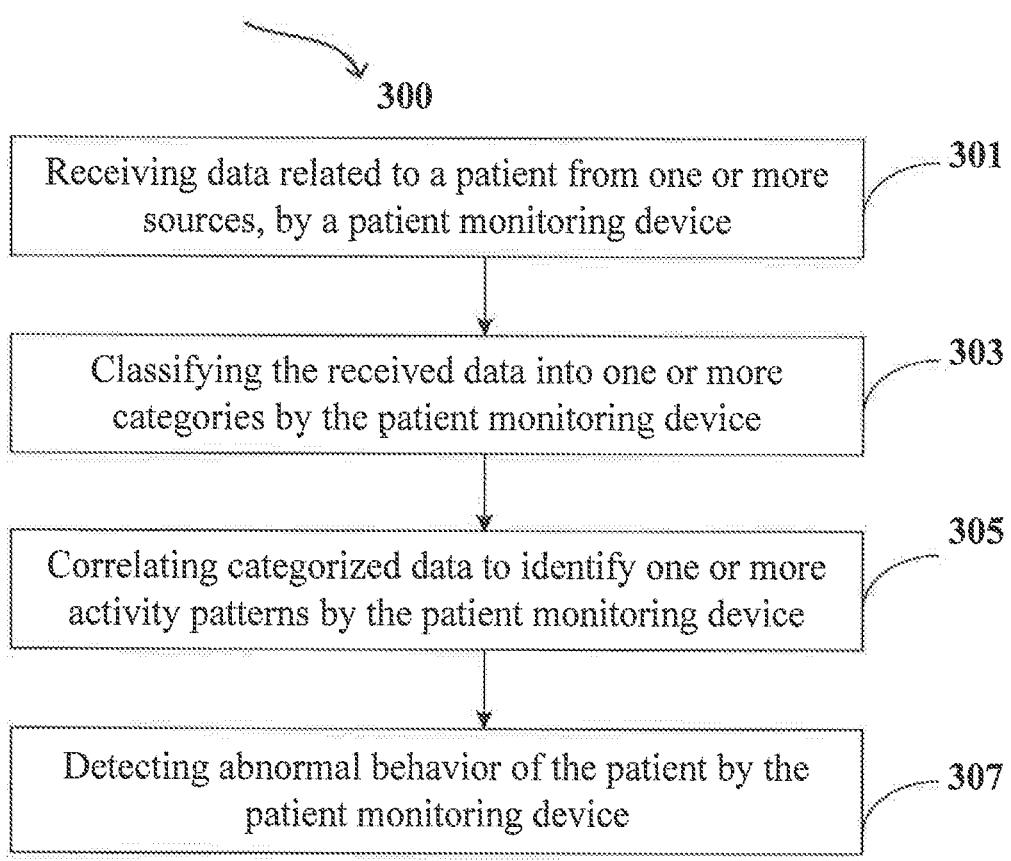
FIG. 3 illustrates a flowchart showing a patient monitoring device for monitoring behaviour of a patient in real-time in accordance with some embodiments of the present disclosure.

FIG. 3 illustrates a flowchart showing a patient monitoring system for monitoring behaviour of a patient in real-time in accordance with some embodiments of the present disclosure.

As illustrated in FIG. 3, the method 300 comprises one or more blocks illustrating a method for monitoring behaviour of a patient in real-time. The method 300 may be described in the general context of computer executable instructions. Generally, computer executable instructions can include routines, programs, objects, components, data structures, procedures, modules, and functions, which perform particular functions or implement particular abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 301, data related to a patient 101 is received from one or more sources 103. In an embodiment, a processor 203 configured in the patient monitoring device 107 receives the data related to a patient 101 from one or more sources 103, wherein the one or more sources 103 are at least one of an audio recording device, an image capturing device, a video capturing device and one or more medical devices. In one embodiment, data may include, hint not limited to audio data 209, video data 211, image data 213, medical data 215 and patient data 217.

At block 303, the received data is classified into one or more categories. In an embodiment, the processor 203 classifies the received data into one or more categories based on one or more rules stored in a memory 207 configured in the patient monitoring device 107. The one or more rules are either predefined or dynamically updated. The one or more categories may be an audio category, video category, image category and medical category. In medical category, the medical reports are further categorized based on the type of the report, such as ECG report, Blood pressure report, blood-sugar level report etc. Classifying the data further comprises filtering the data after categorisation, based on one or more rules, wherein filtering is a process of retaining the data required for monitoring the behaviour of the patient 101 and discarding rest of the data.

At block 305, the categorized data is correlated to identify one or more activity patterns. In an embodiment, the processor 203 correlates the categorized data i.e. the audio data 209, the video data 211, the image data 213 and the medical data 215 to identify the one or more activity patterns of the patient 101. The categorized data is converted into text format based on predefined configuration information stored in the memory 207, since correlation of the categorized data can be performed only when the data related to the patient 101 is in a single format. Upon correlating the data, one or more activity patterns corresponding to the patient 101 are identified. Each of the one or more activity patterns are associated with an activity performed by the patient 101 at predefined time intervals. In one embodiment, the one or more activity patterns may be food intake patterns, medicine intake patterns, breathing pattern, sleeping patterns etc.

At block 307, abnormal behaviour of the patient 101 is detected. In an embodiment, the processor 203 detects the abnormal behaviour of the patient by comparing the identified one or more activity patterns with one or more predefined activity patterns corresponding to the patient 101, stored in the memory 207. If the identified one or more activity patterns are different from the one or more predefined activity patterns, then the abnormal behaviour of the patient 101 corresponding to the identified indifferent activity pattern is detected and a notification related to the abnormal behaviour of the patient 101 is provided to the one or more receiving entities. As an example one or more receiving entities may include, but not limited to, one or more caretakers of the patient 101 such as the doctor, a nurse, friend of the patient, relatives of the patient etc.

Figure 4:
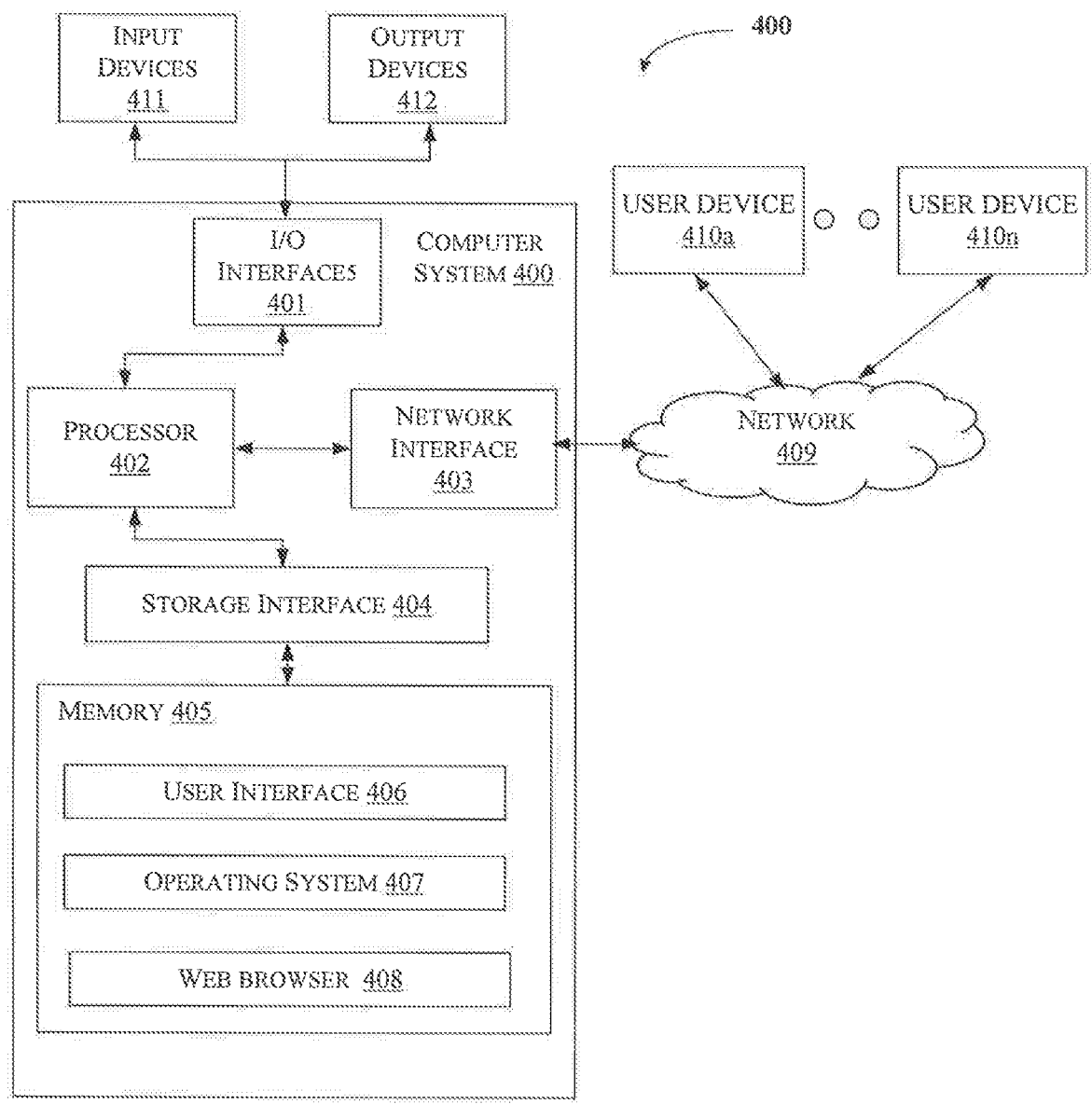
FIG. 4 is a block diagram of an exemplary computer system for implementing embodiments consistent with the present disclosure.

FIG. 4 is a block diagram of an exemplary computer system for implementing embodiments consistent with the present disclosure.

In an embodiment, the computer system 400 is used to improve performance of products based on user behaviour with the products using a patient monitoring device 107. The computer system 400 may comprise a central processing unit ("CPU" or "processor") 402. The processor 402 may comprise at least one data processor for executing program components for executing user- or system-generated business processes. A user may include a person, a person using a device such as such as those included in this invention, or such a device itself. The processor 402 may include specialized processing units such as integrated system (bus) controllers, memory management control units, floating point units, graphics processing units, digital signal processing units, etc.

The processor 402 may be disposed in communication with one or more input/output (I/O) devices (411 and 412) via I/O interface 401. The I/O interface 401 may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n/big/nix, Bluetooth, cellular (e.g., Code-Division Multiple Access (CDMA), High-Speed Packet Access (HSPA+), Global System For Mobile Communications (GSM), Long-Term Evolution (LTE), WiMax, or the like), etc.

Using the I/O interface 401, the computer system 400 may communicate with one or more I/O devices (411 and 412).

In some embodiments, the processor 402 may be disposed in communication with a communication network 409 via a network interface 403, The network interface 403 may communicate with the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE 802.11a/big/nix, etc. Using the network interface 403 and the communication network 409, the computer system 400 may communicate with one or more user devices 410 (a, . . . , n). The communication network 409 can be implemented as one of the different types of networks, such as intranet or Local Area Network (LAN) and such within the organization. The communication network 409 may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 409 may include a variety of network devices, including routers, bridges, servers, computing devices, storage devices, etc. The one or more user devices 410 (a, . . . , n) may include, without limitation, personal computer(s), mobile devices such as cellular telephones, smartphones, tablet computers, eBook readers, laptop computers, notebooks, gaming consoles, or the like.

In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user interface application 406, an operating system 407, web browser 408 etc. In some embodiments, computer system 400 may store user/application data 406, such as the data, variables, records, etc., as described in this invention. Such databases may be implemented as fault-tolerant, relational, scalable, secure databases such as Oracle or Sybase.

The operating system 407 may facilitate resource management and operation of the computer system 400. Examples of operating systems include, without limitation, Apple Macintosh OS X, UNIX, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), international Business Machines (IBM) OS/2, Microsoft Windows (XP, Vista/

7/8, etc.), Apple iOS, Google Android, Blackberry Operating System (OS), or the like. User interface 406 may facilitate display, execution, interaction, manipulation, or operation of program components through textual or graphical facilities. For example, user interfaces may provide computer interaction interface elements on a display system operatively connected to the computer system 400, such as cursors, icons, check boxes, menus, smilers, windows, widgets, etc. Graphical User Interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 400 may implement a web browser 408 stored program component. The web browser may be a hypertext viewing application, such as Microsoft Internet Explorer, Google Chrome, Mozilla Firefox, Apple Safari, etc. Secure web browsing may be provided using Secure Hypertext Transport Protocol (HTIPS) secure sockets layer (SSL), Transport Layer Security (TLS), etc. Web browsers may utilize facilities such as AJAX, DHTML, Adobe Flash, JavaScript, Java, Application Programming interfaces (APIs), etc. In some embodiments, the computer system 400 may implement a mail server stored program component. The mail server may be an Internet mail server such as Microsoft Exchange, or the like. The mail server may utilize facilities such as Active Server Pages (ASP), ActiveX, American National Standards Institute (ANSI) C++/C #, Microsoft .NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 400 may implement a mail client stored program component. The mail client may be a mail viewing application, such as Apple Mail, Microsoft Entourage, Microsoft Outlook, Thunderbird, etc.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Advantages of the Embodiment of the Present Disclosure are Illustrated Herein

In an embodiment, the present disclosure provides a method for monitoring behaviour of a patient in real-time using a patient monitoring device.

The present disclosure discloses a method wherein the data related to patient, which is obtained from one or more sources, are correlated to identify abnormal behaviour of the patient.

The present disclosure provides a feature wherein a notification regarding the abnormal behaviour is provided to one or more receiving entities along with the one or more remedies to take immediate action on the patient.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The specification has described a method and a system to monitor behaviour of the patient in real-time using a patient monitoring device. The illustrated steps are set out to explain the exemplary embodiments shown, and it should be anticipated that on-going technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

REFERRAL NUMERALS

| Reference Number | Description |
| --- | --- |
| 100 | Architecture |
| 101 | Patient |
| $103_1, 103_2, 103_3, \ldots 103_n$ | One or more sources |
| 105 | Communication network |
| 107 | Patient monitoring device |
| 109 | Hospital systems |
| 111 | One or more medical repositories |
| 203 | Processor |
| 205 | User interface |
| 207 | Memory |
| 208 | Data |
| 209 | Audio data |
| 211 | Video data |
| 213 | Image data |
| 215 | Medical data |
| 217 | Patient data |
| 219 | Predefined activity pattern data |
| 220 | Symptom learning table |
| 221 | Remedy data |
| 222 | Rules data |
| 223 | Other data |
| 224 | Modules |
| 225 | Receiving module |
| 227 | Classifying module |
| 228 | Analysing module |
| 229 | Correlating module |
| 231 | Pattern recognizing module |
| 233 | Detecting module |
| 235 | Alerting module |
| 237 | Comparing module |
| 239 | Indicating module |
| 241 | Other modules |

What is claimed is:

1. A method for monitoring behaviour of a patient in real-time, the method comprising:
   receiving, by a patient monitoring device comprising a processor and a memory, data related to an activity performed by the patient from one or more sources;
   classifying, by the patient monitoring device, the received data into one or more categories based on one or more rules,
      wherein the one or more rules categorize the received data into the one or more categories that comprise an audio category, a video category, an image category, and a medical category, and wherein the one or more rules further define different formats in which the one or more categories of the received data are to be processed by the patient monitoring device;
   filtering, by the patient monitoring device, the classified data based on one or more rules to identify one or more relevant data required for monitoring the behaviour of the patient in real-time,
      wherein the filtering of the data comprises processing the classified data based on the one or more rules to discard data indicative of an expected activity, and
      wherein the one or more rules are dynamically updated based on the activity performed by the patient and a time consumed to perform the activity;
   converting, by the patient monitoring device, the one or more relevant data from the different formats into a text format based on predefined configuration information stored in the memory;
   correlating, by the patient monitoring device, the one or more relevant data in the text format to identify one or more activity patterns corresponding to the patient, by performing text analytics technique in combination with one or more machine learning algorithms, wherein each of the one or more activity patterns are associated with the activity performed by the patient at predefined time intervals;
   detecting, by the patient monitoring device, abnormal behaviour that affect recovery of the patient if the one or more identified activity patterns are different from one or more predefined activity patterns corresponding to the patient;
   identifying, by the patient monitoring device, one or more remedies for the detected abnormal behaviour of the patient; and
   generating, by the patient monitoring device, an alert notification of the detected abnormal behavior, wherein the alert notification along with the one or more remedies are provided to one or more receiving entities for taking an immediate remedy action on the patient.

2. The method as claimed in claim 1, further comprising:
   comparing, by the patient monitoring device, the abnormal behaviour of the patient with a symptom learning table, to identify one or more symptoms corresponding to the abnormal behaviour of the patient, wherein each of the one or more symptoms is associated with a precaution measure; and
   indicating, by the patient monitoring device, the precaution measure corresponding to the identified symptom to one or more receiving entities.

3. The method as claimed in claim 2, wherein the symptom learning table is extracted from one or more medical repositories associated with the patient monitoring system.

4. The method as claimed in claim 1, wherein the received data is at least one of audio data, video data, image data, medical data and patient data.

5. The method as claimed in claim 1, wherein the one or more sources are at least one of audio recording device, video capturing device, image capturing device and one or more medical devices.

6. The method as claimed in claim 1, wherein the activity comprises a voluntary activity performed by the patient.

7. A patient monitoring device for monitoring behaviour of a patient in real-time, the patient monitoring device comprising:
   a processor; and
   a memory communicatively coupled to the processor, wherein the memory stores the processor-executable instructions, which, on execution, causes the processor to:
      receive data related to an activity performed by the patient from one or more sources;
      classify the received data into one or more categories based on one or more rules, wherein the one or more rules categorize the received data into the one or more categories that comprise an audio category, a video category, an image category, and a medical category, and wherein the one or more rules further define different formats in which the one or more categories of the received data are to be processed by the patient monitoring device;
      filter the classified data based on one or more rules to identify one or more relevant data required for monitoring the behaviour of the patient in real-time, wherein the filtering of the data comprises processing the classified data based on the one or more rules to discard data indicative of an expected activity, and wherein the one or more rules are dynamically updated based on the activity performed by the patient and a time consumed to perform the activity;

convert the one or more relevant data from the different formats into a text format based on predefined configuration information stored in the memory;

correlate the one or more relevant data in the text format to identify one or more activity patterns corresponding to the patient, by performing text analytics technique in combination with one or more machine learning algorithms, wherein each of the one or more activity patterns are associated with the activity performed by the patient at predefined time intervals;

detect abnormal behaviour that affect recovery of the patient if the one or more identified activity patterns are different from one or more predefined activity patterns corresponding to the patient;

identify one or more remedies for the detected abnormal behaviour of the patient; and generate an alert notification of the detected abnormal behavior, wherein the alert notification along with the one or more remedies are provided to one or more receiving entities for taking an immediate remedy action on the patient.

8. The patient monitoring device as claimed in claim 7, wherein the processor is further configured to:

compare the abnormal behaviour of the patient with a symptom learning table, to identify one or more symptoms corresponding to the abnormal behaviour of the patient, wherein each of the one or more symptoms is associated with a precaution measure; and indicate the precaution measure corresponding to the identified symptom to one or more receiving entities.

9. The patient monitoring device as claimed in claim 8, wherein the processor is configured to extract symptom learning table from one or more medical repositories associated with the patient monitoring system.

10. The patient monitoring device as claimed in claim 7, wherein the received data is at least one of audio data, video data, image data, medical data and patient data.

11. The patient monitoring device as claimed in claim 7, wherein the one or more sources are at least one of audio recording device, video capturing device, image capturing device and one or more medical devices.

12. A non-transitory computer readable medium including instructions stored thereon that when processed by at least one processor causes a patient monitoring device to perform operations comprising:

receiving data related to an activity performed by the patient from one or more sources;

classifying the received data into one or more categories based on one or more rules stored in a memory associated to a patient monitoring system, wherein the one or more rules categorize the received data into the one or more categories that comprise an audio category, a video category, an image category, and a medical category, and wherein the one or more rules further define different formats in which the one or more categories of the received data are to be processed by the patient monitoring device;

filtering the classified data based on one or more rules to identify one or more relevant data required for monitoring the behaviour of the patient in real-time, wherein the filtering of the data comprises processing the classified data based on the one or more rules to discard data indicative of an expected activity, and wherein the one or more rules are dynamically updated based on the activity performed by the patient and a time consumed to perform the activity;

converting the one or more relevant data from the different formats into a text format based on predefined configuration information stored in the memory;

correlating the one or more relevant data in the text format to identify one or more activity patterns corresponding to the patient, by performing text analytics technique in combination with one or more machine learning algorithms, wherein each of the one or more activity patterns are associated with the activity performed by the patient at predefined time intervals;

detecting abnormal behaviour that affect recovery of the patient if the one or more identified activity patterns are different from one or more predefined activity patterns corresponding to the patient;

identifying one or more remedies for the detected abnormal behaviour of the patient; and generating an alert notification of the detected abnormal behavior, wherein the alert notification along with the one or more remedies are provided to one or more receiving entities for taking an immediate remedy action on the patient.

* * * * *